US010292993B2

(12) United States Patent
Choi et al.

(10) Patent No.: US 10,292,993 B2
(45) Date of Patent: May 21, 2019

(54) METHOD OF INHIBITING QUORUM SENSING USING D-GALACTOSE

(71) Applicants: Seoul National University R&DB Foundation, Seoul (KR); Foundation of Soongsil University—Industry Cooperation, Seoul (KR)

(72) Inventors: Bong Kyu Choi, Seoul (KR); Eun Ju Ryu, Incheon (KR); Jae Hyun Sim, Paju (KR); Byeong Moon Kim, Seoul (KR); Julian Lee, Seoul (KR); Jun Sim, Incheon (KR)

(73) Assignees: SEOUL NATIONAL UNIVERSITY R&DB FOUNDATION, Seoul (KR); FOUNDATION OF SOONGSIL UNIVERSITY-INDUSTRY COOPERATION, Seoul (KR)

( * ) Notice: Subject to any disclaimer, the term of this patent is extended or adjusted under 35 U.S.C. 154(b) by 0 days.

(21) Appl. No.: 14/860,813

(22) Filed: Sep. 22, 2015

(65) Prior Publication Data

US 2016/0082023 A1     Mar. 24, 2016

Related U.S. Application Data

(60) Provisional application No. 62/054,431, filed on Sep. 24, 2014.

(51) Int. Cl.
*A61K 31/7004* (2006.01)
*A61P 31/04* (2006.01)

(52) U.S. Cl.
CPC .......... *A61K 31/7004* (2013.01); *A61P 31/04* (2018.01); *Y02A 50/481* (2018.01)

(58) Field of Classification Search
None
See application file for complete search history.

(56) References Cited

FOREIGN PATENT DOCUMENTS

| EP | 0184121 | * | 6/1986 | ............. A23L 29/30 |
|---|---|---|---|---|
| JP | S55-69507 | * | 5/1980 | ............... A61K 7/16 |
| JP | 2005-520807 | | 7/2005 | |
| JP | 2013-010724 | * | 1/2013 | ............... A61K 8/80 |
| KR | 10-2006-0075868 | | 7/2006 | |
| KR | 10-2013-0106837 | | 9/2013 | |
| KR | 10-2014-0061349 | | 5/2014 | |
| WO | 2008/076461 | | 6/2008 | |
| WO | WO2014/127066 | * | 8/2014 | ........... A61K 31/198 |

OTHER PUBLICATIONS

Merriam-Webster's Collegiate Dictionary, published 1998 by Merriam-Webster incorporated, p. 924.*
English machine translation of EP0184121, published 1986, downloaded from translationportal.epo.org.*
English machine translation of S55-69507 above, (May 1980) downloaded from translationportal.epo.org.*
English machine translation of JP2013-010724 above (Jan. 2013) downloaded from translationportal.epo.og.*
Gutierrez et al., "L-Galactose as a natural product: isolation from a marine octocoral of the first a-L-galactosyl saponin" Tetrahedron Letters (2004) vol. 45 pp. 7833-7836.*
Chemical Abstracts Registry #15572-79-9 "L-galactose" entered 1984, from STN file Registry.*
Chemical Abstracts Registry #59-23-4 "D-galactose" entered 1984, from STN file Registry.*
Blackmond et al., "The Origin of Biological Homochirality" Cold Spring Harb Perspect Biol (2010) voll. 2 pp. 1-17.*
Levin et al., "L-Sugars: Lev-O-Cal(TM)" im Alternative Sweeteners, Second Edition Revised and Expanded, copyright 1991 by Marcel Dekker, Inc, chapter 7 pp. 117-125.*
Lu et al., "Removal and prevention of dental plaque with D-tagatose" International Journal of Cosmetic Science vol. 24 pp. 225-234 (Year: 2002).*
Kolenbrander, Paul E. "Coaggregations among Oral Bacteria" Methods in Enzymology vol. 253 pp. 385-397 (Year: 1995).*
Kolenbrander, P. E., et al., "Inhibition of coaggregation between Fusobacterium nucleatum and Porphyromonas (Bacteroides) gingivalis by lactose and related sugars", Infection and Immunity, Oct. 1989, vol. 57, No. 10, pp. 3204-3209.
Jang, Y. J., et al., "Autoinducer 2 of Fusobacterium nucleatum as a target molecule to inhibit biofilm formation of periodontopathogens", Archives of Oral Biology, Jan. 2013, vol. 58, pp. 17-27.
International Search Report and the Written Opinion, Patent Cooperation Treaty, dated Dec. 22, 2015, International Application No. PCT/KR2015/009948.
Graciela Rosen et al. ,Infection and Immunity, "Actinobacillus actinomycetemcomitans Serotype b Lipopolysaccharide Mediates Coaggregation with Fusobacterium nucleatum", Jun. 2003, p. 3652-3656 vol. 71, No. 6.
Graciela Rosen et al, Federation of European Microbiological Societies Research Letter, "Coaggregation of Treponema denticola with Porphyromonas gingivalis and Fusobacteriumnucleatum ismediated by themajor outer sheath protein of Treponema denticola", Oct. 2008, p. 59-66.
Paul E. Kolenbrander, et al., 'Inhibition of Coaggregation between Fusobacterium nucleatum and Porphyromonas (Bacteroides) gingivalis by Lactose and Related Sugars', Infection and Immunity, Oct. 1989, 57, 3204-3209.
Yun-ji Jang, et al., 'Autoinducers 2 of Fusobacterium nucleatum as a target molecule to inhibit biofiim formation of periodontopathogenes', Archives of Oral Biology, Jan. 2013, 58, 17-27.

(Continued)

Primary Examiner — Eric Olson
(74) Attorney, Agent, or Firm — Lex IP Meister, PLLC

(57) ABSTRACT

Provided are a use of D-galactose in inhibition of quorum sensing and/or in prevention and/or treatment of oral bacterial diseases; in particular, a composition for inhibiting quorum sensing and a composition for preventing and/or treating oral bacterial diseases, the composition comprising D-galactose, and a method of inhibiting quorum sensing and a method of preventing and/or treating oral bacterial diseases, the method comprising administering D-galactose.

6 Claims, 11 Drawing Sheets

(56) References Cited

OTHER PUBLICATIONS

Kimberly A. Mencl at al., "Wound biofilms: Lessons learned from oral biofilms", Perspective Article, Wound Repair and Regeneration, 2013, 21, pp. 352-362, the Wound Healing Society.

A. Saito et al., "Fusobacteriumnucleatum enhances invasion of human gingival epithelial and aortic endothelial cells byPorphyromonas gingivalis", FEMS Immunol Med Microbiol, 54, p. 349-355, 2008.

* cited by examiner

METHOD OF INHIBITING QUORUM SENSING USING D-GALACTOSE

CROSS-REFERENCE TO RELATED APPLICATIONS

This application claims the benefit of Provisional Application No. 62/054,431 filed on Sep. 24, 2014 in the United States Patent and Trademark Office, the entire disclosure of which is hereby incorporated by reference.

BACKGROUND OF THE INVENTION

1. Field

The present disclosure relates to a use of D-galactose in inhibition of quorum sensing and/or in prevention and/or treatment of oral bacterial diseases. In particular, provided are a composition for inhibiting quorum sensing and a composition for preventing and/or treating oral bacterial diseases, the composition comprising D-galactose; and a method of inhibiting quorum sensing and a method of preventing and/or treating oral bacterial diseases, the method comprising administering D-galactose.

2. Description of the Related Art

Dental caries and periodontal disease are representative oral diseases and are the main causes of tooth extraction. There have been many trials to effectively prevent and treat these diseases, but many restrictions still remain.

Antibiotics function to directly remove bacteria causing dental caries and periodontal diseases, but they also kill the beneficial bacteria and long-term use thereof is difficult because of the problem of resistance, etc. It is difficult to expect substantial effects of the materials, such as corn unsaponifiable fraction extract used as a therapeutic agent for periodontal diseases in some countries, on moderate to severe periodontal diseases, and their efficacy still remains controversial. Like antibiotics, mouthwashes worldwidely used have non-specific antiseptic action and also contain alcohol, and thus there is a risk of causing oral cancer and dry mouth.

Resent experimental results have reported that dental caries as well as periodontal disease are caused by not a single species of microorganisms, but mediated by signal transduction systems between various microorganisms. When the number of signaling molecules secreted by bacteria reaches the critical number, that is, quorum, bacteria sense the quorum sensing molecules, which induce biofilm formation and virulence. Currently known quorum sensing molecules are autoinducer-1 (AI-1), autoinducer-2 (AI-2), and oligopeptides. AI-1 is used for intra-species communication and AI-2 is a universal signal for interspecies communications, and plays an important role in biofilm formation and expression of virulence factors.

When these features of the virulent bacteria are utilized, therapeutic agents for oral diseases can be developed to effectively control dental caries and periodontal diseases. In other words, a drug which is able to effectively inhibit quorum sensing inducing biofilm formation and virulence without direct killing of bacteria is developed to provide a superior prophylactic or therapeutic agent having no disadvantages of the current therapeutic agents.

Since quorum sensing inhibitors do not directly kill bacteria, no resistance occurs and thus their long-term use is possible. Further, since quorum sensing inhibitors do not act against specific bacteria but interfere with communication between bacteria, they show broad spectrum of applications. When quorum sensing inhibitors are used together with antibiotics, they help actions of the antibiotics. Thus, although antibiotic is used in a small amount, great effects can be obtained. Owing to these advantages of quorum sensing inhibitors, they can be next-generation prophylactic or therapeutic agents capable of effectively controlling periodontal diseases.

Currently available quorum sensing inhibitors may be selected from chemicals synthesized using lead compounds such as furanones or homoserine lactones, peptide-like mimics, and a type of sugar, D-ribose. However, there have been no materials used as quorum sensing inhibitors in medical drugs or products. For industrialization of quorum sensing inhibitors, efficacy of substantially inhibiting quorum sensing in the human body and safety of being harmless to the human body in spite of their long-term use must be proven. The synthetic chemicals exhibit excellent inhibitory efficacy on quorum sensing, but in some cases, their safety has not been secured in a toxicity test, an animal test, and a clinical test. A type of sugar, D-ribose has no safety problem because it has been used for a long period of time, but its inhibitory efficacy is much lower than those of the synthetic chemicals.

Accordingly, there is a need for the development of a quorum sensing inhibitor having excellent inhibitory efficacy on quorum sensing and also securing safety.

BRIEF SUMMARY OF THE INVENTION

Provided is a use of D-galactose relating to quorum sensing inhibitory activity.

Specifically, an embodiment provides a composition for inhibiting bacterial quorum sensing, the composition comprising a pharmaceutically effective amount of D-galactose.

Another embodiment provides a method of inhibiting bacterial quorum sensing, the method comprising administering a pharmaceutically effective amount of D-galactose into a subject in need of inhibition of bacterial quorum sensing.

Still another embodiment provides a use of D-galactose for inhibition of bacterial quorum sensing.

Still another embodiment provides a use of D-galactose for production of bacterial quorum sensing inhibitors.

Still another embodiment provides a composition for inhibiting bacterial biofilm formation, the composition comprising a pharmaceutically effective amount of D-galactose.

Still another embodiment provides a method of inhibiting bacterial biofilm formation, the method comprising administering a pharmaceutically effective amount of D-galactose into a subject in need of inhibition of bacterial biofilm formation.

Still another embodiment provides use of D-galactose for inhibition of bacterial biofilm formation.

Still another embodiment provides use of D-galactose for production of bacterial biofilm formation inhibitors.

Still another embodiment provides a pharmaceutical composition for preventing and/or treating oral bacterial diseases, the composition comprising a pharmaceutically effective amount of D-galactose.

Still another embodiment provides a food composition for preventing and/or ameliorating oral bacterial diseases, the composition comprising D-galactose.

Still another embodiment provides a method of preventing and/or treating and/or ameliorating oral bacterial diseases, the method comprising administering a pharmaceutically effective amount of D-galactose into a subject in need of preventing and/or treating or ameliorating oral bacterial diseases.

Still another embodiment provides a use of D-galactose for preventing and/or treating and/or ameliorating oral bacterial diseases.

Still another embodiment provides a use of D-galactose for preparation of a composition for preventing and/or treating and/or ameliorating oral bacterial diseases.

In the composition, method and/or use for prevention and/or treatment, the oral bacterial disease may be dental caries or periodontal disease (e.g., periodontitis, gingivitis, etc.).

DETAILED DESCRIPTION OF THE INVENTION

Figure 1:
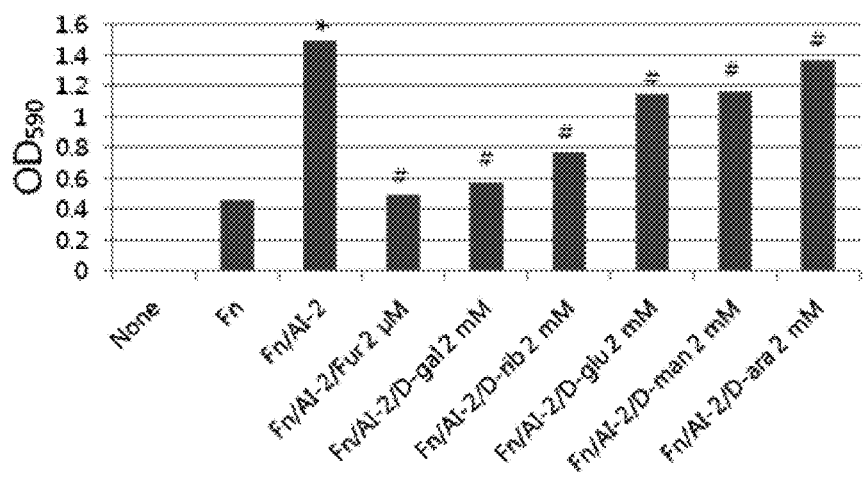
FIG. 1 is a graph showing results of crystal violet staining to examine inhibitory effects of quorum sensing inhibitor candidates on *F. nucleatum* (Fn) biofilm formation induced by Fn AI-2 (*: showing a statistical significance, compared to Fn biofilm (indicated by 'Fn') ($p<0.05$); #: showing a statistical significance, compared to biofilm (indicated by 'Fn/AI-2') formed by addition of AI-2 to Fn ($p<0.05$))

D-galactose is one of sugars found in milk. Lactose makes up around 2~8% of milk, and is broken down into monosaccharides, glucose and D-galactose. D-galactose is a natural substance that has been used for a long period of time, and its industrialization is possible once its efficacy is proven. This specification demonstrates that D-galactose has quorum sensing inhibitory efficacy twice higher than that of D-ribose which is known to have quorum sensing inhibitory efficacy, thereby suggesting use of D-galactose as a quorum sensing inhibitor.

Quorum sensing (QS) is a bacterial cell-cell communication process, which not only induces biofilm formation, but also increases virulence. A quorum sensing inhibitor is a promising next-generation antibiotic which overcomes limitations of current antibiotics and effectively controls oral diseases such as dental caries, periodontal infection, etc. Therefore, this specification suggests use of D-galactose as a therapeutic agent for oral bacterial diseases (or oral inflammatory diseases), in which D-galactose has a quorum sensing inhibitor effect to overcome limitations of antibiotics.

First, an aspect provides a composition for inhibiting bacterial quorum sensing, the composition comprising a pharmaceutically effective amount of D-galactose.

Another aspect provides a method of inhibiting bacterial quorum sensing, the method comprising administering a pharmaceutically effective amount of D-galactose into a subject in need of inhibition of bacterial quorum sensing.

Still another aspect provides use of D-galactose for inhibition of bacterial quorum sensing.

Still another aspect provides use of D-galactose for production of bacterial quorum sensing inhibitors.

The bacteria may be oral disease-causing bacteria. The oral disease-causing bacteria may be one or more, for example, one, two or more, or three or more selected from the group consisting of periodontal disease-causing bacteria such as bacteria belonging to the genus *Fusobacterium* (e.g., *Fusobacterium nucleatum*, etc.), bacteria belonging to the genus *Porphyromonas* (e.g., *Porphyromonas gingivalis*, etc.), bacteria belonging to the genus *Tannerella* (e.g., *Tannerella forsythia*, etc.), bacteria belonging to the genus *Aggregatibacter* (e.g., *Aggregatibacter actinomycetemcomitans*, etc.), bacteria belonging to the genus *Treponema* (e.g., *Treponema denticola*, etc.), bacteria belonging to the genus *Prevotella* (e.g., *Prevotella intermedia*, etc.); and cariogenic bacteria such as bacteria belonging to the genus *Streptococcus* (e.g., *Streptococcus mutans, Streptococcus sobrinus*, etc.).

As described above, when the number of signaling molecules secreted by bacteria reaches the critical number, that is, Quorum, which is sensed by the bacteria (Quorum Sensing, QS), quorum sensing autoinducers (AI) are secreted and detected by bacteria, resulting in biofilm formation and virulence. Therefore, when quorum sensing autoinducers are inhibited, quorum sensing may be inhibited, resulting in inhibition of biofilm formation and virulence. The quorum sensing autoinducers may be selected from Autoinducer-1 (AI-1) used for intra-species communication, Autoinducer-2 (AI-2) used for inter-species communication (i.e., acting on different species) as well as intra-species communication (i.e., acting on the same species), peptide-based quorum sensing autoinducer, and the like. Among them, AI-2 is a universal signal which acts on inter-species communication as well as intra-species communication, and plays an important role in biofilm formation and expression of virulence factors.

As demonstrated in Example 7 of this specification, D-galactose has an excellent inhibitory effect on AI-2 activity.

Therefore, still another aspect provides a composition for inhibiting bacterial quorum sensing autoinducers, the composition comprising a pharmaceutically effective amount of D-galactose.

Still another aspect provides a method of inhibiting bacterial quorum sensing autoinducers, the method comprising administering a pharmaceutically effective amount of D-galactose into a subject in need of inhibition of bacterial quorum sensing autoinducers.

Still another aspect provides use of D-galactose for inhibition of bacterial quorum sensing autoinducers.

Still another aspect provides use of D-galactose for production of inhibitors of bacterial quorum sensing autoinducers.

The quorum sensing autoinducer may be Autoinducer-1 (AI-1), Autoinducer-2 (AI-2), or a mixture thereof, and for example, AI-2. The quorum sensing autoinducers may be derived (separated) from oral diseases-causing bacteria. For example, the quorum sensing autoinducers may be derived (separated) from one or more, for example, one, two or more, or three or more selected from the group consisting of periodontal disease-causing bacteria such as bacteria belonging to the genus *Fusobacterium* (e.g., *Fusobacterium nucleatum*, etc.), bacteria belonging to the genus *Porphyromonas* (e.g., *Porphyromonas gingivalis*, etc.), bacteria belonging to the genus *Tannerella* (e.g., *Tannerella forsythia*, etc.), bacteria belonging to the genus *Aggregatibacter* (e.g., *Aggregatibacter actinomycetemcomitans*, etc.), bacteria belonging to the genus *Treponema* (e.g., *Treponema denticola*, etc.), bacteria belonging to the genus *Prevotella* (e.g., *Prevotella intermedia*, etc.); and cariogenic bacteria such as bacteria belonging to the genus *Streptococcus* (e.g., *Streptococcus mutans, Streptococcus sobrinus*, etc.). In an embodiment, the quorum sensing autoinducer may be AI-2 derived from *Fusobacterium nucleatum*, but are not limited thereto.

As described above, bacterial biofilm formation may be inhibited by inhibiting the quorum sensing autoinducers.

Therefore, still another aspect provides a composition for inhibiting bacterial biofilm formation, the composition comprising a pharmaceutically effective amount of D-galactose.

Still another aspect provides a method of inhibiting bacterial biofilm formation, the method comprising administering a pharmaceutically effective amount of D-galactose into a subject in need of inhibition of bacterial biofilm formation.

Still another aspect provides use of D-galactose for inhibition of bacterial biofilm formation.

Still another aspect provides use of D-galactose for production of bacterial biofilm formation inhibitors.

The biofilm may be formed by one or more, for example, one, two or more, or three or more selected from the group consisting of periodontal disease-causing bacteria such as bacteria belonging to the genus *Fusobacterium* (e.g., *Fusobacterium nucleatum*, etc.), bacteria belonging to the genus *Porphyromonas* (e.g., *Porphyromonas gingivalis*, etc.), bacteria belonging to the genus *Tannerella* (e.g., *Tannerella forsythia*, etc.), bacteria belonging to the genus *Aggregatibacter* (e.g., *Aggregatibacter actinomycetemcomitans*, etc.), bacteria belonging to the genus *Treponema* (e.g., *Treponema denticola*, etc.), bacteria belonging to the genus *Prevotella* (e.g., *Prevotella intermedia*, etc.); and cariogenic bacteria such as bacteria belonging to the genus *Streptococcus* (e.g., *Streptococcus mutans, Streptococcus sobrinus*, etc.).

Since biofilm formation by bacteria is associated with virulence, virulence of pathogenic bacteria may be reduced by the inhibitory effect on biofilm formation, and oral bacterial diseases associated with the pathogenic bacteria may be prevented and/or treated.

Therefore, still another aspect provides a pharmaceutical composition for preventing and/or treating oral bacterial diseases, the composition comprising a pharmaceutically effective amount of D-galactose.

Still another aspect provides a food composition for preventing and/or ameliorating oral bacterial diseases, the composition comprising D-galactose. The food composition may be one or more selected from the group consisting of a variety of foods, drinks, food additives, etc.

Still another aspect provides a method of inhibiting oral bacterial disease-causing bacteria, the method comprising administering a pharmaceutically effective amount of D-galactose into a subject in need of inhibition of oral bacterial disease-causing bacteria. The subject may be a subject in need of reducing virulence of oral bacterial disease-causing bacteria, and the inhibition method may be a method of reducing virulence of oral bacterial disease-causing bacteria.

Still another aspect provides a method of preventing and/or treating and/or ameliorating oral bacterial diseases, the method comprising administering a pharmaceutically effective amount of D-galactose into a subject in need of preventing and/or treating or ameliorating oral bacterial diseases.

Still another aspect provides use of D-galactose for preventing and/or treating or ameliorating of oral bacterial diseases.

Still another aspect provides use of D-galactose for preparation of a composition for preventing and/or treating and/or ameliorating oral bacterial diseases.

The oral bacterial disease may be an oral bacterial disease, for example, dental caries or periodontal disease (e.g., periodontitis, gingivitis, etc.). The oral bacterial disease-causing bacteria may be one or more, for example, one, two or more, or three or more selected from the group consisting of periodontal disease-causing bacteria such as bacteria belonging to the genus *Fusobacterium* (e.g., *Fusobacterium nucleatum*, etc.), bacteria belonging to the genus *Porphyromonas* (e.g., *Porphyromonas gingivalis*, etc.), bacteria belonging to the genus *Tannerella* (e.g., *Tannerella forsythia*, etc.), bacteria belonging to the genus *Aggregatibacter* (e.g., *Aggregatibacter actinomycetemcomitans*, etc.), bacteria belonging to the genus *Treponema* (e.g., *Treponema denticola*, etc.), bacteria belonging to the genus *Prevotella* (e.g., *Prevotella intermedia*, etc.); and cariogenic bacteria such as bacteria belonging to the genus *Streptococcus* (e.g., *Streptococcus mutans, Streptococcus sobrinus*, etc.).

In the composition, method, and/or use proposed in the present specification, the active ingredient, D-galactose is characterized in that it does not exhibit the inhibitory effects, such as quorum sensing inhibition, inhibition of quorum sensing autoinducers, and inhibition of biofilm formation, against (non-pathogenic) normal oral flora. The normal oral flora is usually present in the oral cavity, but is non-pathogenic and involved in oral immunity in some cases. In the composition, method, and/or use proposed in the present specification, therefore, D-galactose is used as an active ingredient to selectively inhibit the above-described oral disease-causing bacteria without inhibiting normal oral flora, thereby maintaining oral health and exhibiting the effects of preventing and/or treating oral diseases. The normal oral flora may be one or more selected from the group consisting of *Streptococcus oralis, Streptococcus salivarius*, and *Streotpcoccus mitis*.

In the composition, method, and/or use proposed in the present specification, the amount (content) of the active ingredient, D-galactose may be adjusted depending on a usable form and purpose of use, conditions of a subject of application, and the type and severity of symptoms. For example, the content of D-galactose in the composition may be 0.001 to 50% by weight, 0.001 to 30% by weight, 0.001 to 10% by weight, 0.001 to 5% by weight, or 0.001 to 1% by weight, but is not limited thereto.

Further, an adequate administration dose of the active ingredient may vary depending on the subject's age, body weight, or gender, administration form, health conditions, and disease severity. Also, under the discretion of the physician or pharmacist, it may be administered once or several times per day. For example, the active ingredient may be applied at a dose of 0.0001 to 100 mg/kg or 0.0005 to 50 mg/kg. This application dose is only illustrative of the average dose, and thus it may be increased or decreased depending on individuals.

As used herein, the term "pharmaceutically effective amount" means the content or administration amount of the active ingredient which exhibits the desired pharmacological effects, and may be determined depending on various factors such as the formulation method, administration mode, a subject's age, body weight, and gender, pathological condition, diet, administration time, administration frequency, administration route, excretion rate, and response sensitivity.

The subject to be administered with the active ingredient, D-galactose may be a mammal such as a human, and it may be administered via various routes. The administration mode of the active ingredient may be any administration mode typically used, and for example, it may be oral administration, buccal administration, or non-oral administration such as topical administration to the lesion (e.g., external administration for oral cavity such as buccal mucosa, tooth, gingiva, tongue, etc.). According to a general method, the pharmaceutical composition may be formulated into an oral preparation such as a powder, a granule, a tablet, a capsule, a suspension, an emulsion, a syrup, an aerosol, etc., a parenteral preparation such as a transdermal formulation and a sterile injectable solution, or an external preparation for oral cavity such as buccal mucosa, tooth, gingiva, tongue, etc., such as a solution, a suspension, an emulsion, a paste, a patch, an aerosol, an ointment, a spray, etc.

The composition may further comprise auxiliary substances such as a pharmaceutically acceptable and/or sitologically acceptable and/or physiologically acceptable carrier, excipient, and diluent, in addition to the active ingredient. The carrier, excipient, and diluent comprised in the composition may comprise at least one of lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. Upon formulation, a general diluent or excipient such as a filler, an extender, a binder, a wetting agent, a disintegrating agent, a surfactant or the like may be used. A solid formulation for oral administration comprises a tablet, a pill, a powder, a granule, a capsule, etc., and such a solid formulation may be prepared by mixing the active ingredient with at least one excipient, for example, starch, calcium carbonate, sucrose, lactose, gelatin, etc. Also, in addition to the excipient, lubricants, such as magnesium stearate and talc, may be used. A formulation for oral administration may be a suspension, a liquid for internal use, an emulsion, a syrup, an ointment, or the like, and in addition to a frequently used simple diluent, such as water, liquid paraffin, etc., the formulation may include a variety of excipients for example, a wetting agent, a sweetening agent, an aromatic agent, a preservative, etc. A formulation for parenteral administration or an external administration for oral cavity may comprise at least one of a sterile aqueous solution, a non-aqueous solvent, suspension, an emulsion, a freeze-dried preparation, and a transdermal formulation. As the non-aqueous solvent and the suspension, propylene glycol, polyethylene glycol, vegetable oil such as olive oil, injectable ester such as ethyl oleate or the like may be used.

The content of D-galactose as an active ingredient comprised in the health functional food is not particularly limited according to the type of the food, the desired use, etc., and for example, it may be added in an amount of 0.01 to 15% by weight, based on the total weight of the food, and also added in an amount of 0.02 to 10 g, preferably 0.3 to 1 g, based on 100 ml of the health drink composition.

Still another aspect provides an oral product comprising D-galactose. The oral product may have an effect of preventing and/or ameliorating oral bacterial diseases, for example, dental caries, periodontal disease, etc. The oral product may be one or more selected from the group consisting of toothpastes, breath fresheners, oral sprays, gums, oral ointments, and oral patches.

The oral products may be blended with a proper amount of additive selected from the group consisting of an abrasive, a wetting agent, a binder, a foaming agent, a sweetener, a preservative, an effective agent, a flavor, an acidity regulating agent, a brightening agent generally used according to the type and purpose of use.

For example, the abrasive may be one or more selected from the group consisting of calcium monohydrogen phosphate, precipitated silica, calcium carbonate, hydrated alumina, kaolin, and sodium bicarbonate ($NaHCO_3$), and the content of the abrasive may be 20 to 60% by weight (based on the total weight of the product, hereinafter, the same as above), but is not limited thereto. As the wetting agent, one or more selected from the group consisting of glycerin, sorbitol, non-crystalline sorbitol solution, propylene glycol, polyethylene glycol and xylitol may be used in an amount of 20 to 60% by weight, based on the total weight of the composition, but is not limited thereto. As the binder, one or more selected from the group consisting of carrageenan, xanthan gum, sodium carboxymethylcellulose, carboxyvinyl polymer, sodium alginate, and laponite may be used in an amount of 0.1 to 3.0% by weight, for example, 0.5 to 2.0% by weight, but is not limited thereto. As the foaming agent, one or more selected from the group consisting of anionic surfactant such as sodium laurylsulfate, sodium laurylsarcosinate, etc. and sorbitan fatty acid ester, polyoxyethylene hydrogenated castor oil and polyoxyethylene-polyoxypropylene condensed polymers may be used, and the content of the foaming agent may be 0.5 to 5.0% by weight, for example, 0.5 to 3.5% by weight, but is not limited thereto. As the sweetener, saccharin sodium, aspartam and glycyrrhizic acid may be used singly or in combination of two or more thereof, and the content thereof may be 0.05 to 0.5% by weight, but is not limited thereto. As the preservative, para-oxybenzoic acid ester and sodium benzoate may be used singly or in combination of two or more thereof. As the effective agent, sodium fluoride, sodium monofluorophosphate, stannous fluoride, amine fluorides, chlorhexidine, tranexamic acid, allantoins, caproic acids, polyphosphate, enzymes, herbal extract or the like may be used. As the flavor, peppermint oil, spearmint oil, menthol, carbon, etc. may be mixed in a suitable ratio. As the acidity regulating agent, phosphoric acid, sodium phosphate, citric acid, sodium citrate, succinic acid, sodium succinate, tartaric acid, sodium tartrate or the like may be used, and a preferred pH value is 5 to 8. As the brightening agent, titanium oxide may be used, for example, in an amount of 0.1 to 2% by weight, but is not limited thereto.

As described above, it is suggested that D-galactose has more excellent efficacy than that of D-ribose which is known to have the most excellent activity as the quorum sensing inhibitor among sugars. D-galactose is able to effectively block biofilm formation by quorum sensing of bacteria causing two representative oral diseases, periodontitis and dental caries.

EXAMPLES

Hereafter, the present invention will be described in detail by examples. The following examples are intended merely to illustrate the invention and are not construed to restrict the invention.

Example 1: Bacteria Culture

A periodontal disease-causing bacterium, *F. nucleatum* (ATCC 25586) was cultured in a peptic medium (6 g of peptic digest of animal tissue, 6 g of desiccated beef extract, 5 g of sodium chloride, 14.5 g of pancreatic digest of casein, 2.5 g of sodium phosphate) to be used in a quorum sensing test, *P. gingivalis* (ATCC 33277) was cultured in a brain heart infusion medium supplemented with hemin (10 mg/ml) and vitamin K (0.2 mg/ml), and *T. forsythia* (ATCC 43037) was cultured in a new oral spirochete (NOS) broth (ATCC medium 1494) supplemented with vitamin K (0.2 mg/ml) and N-acetylmuramic acid (0.01 mg/ml). The bacteria were incubated at 37° C. for 2-4 days under anaerobic conditions (5% $H_2$, 10% $CO_2$ and 85% $N_2$). AI-2 reporter strain *Vibrio harveyi* BB170 (ATCC BAA-1117) and AI-2 producing strain *V. harveyi* BB152 (ATCC BAA-1119) were cultured in autoinducer bioassay (AB) medium (ATCC Medium 2746) at 30° C. until OD660 nm=0.7. A cariogenic bacterium, *Streptococcus mutans* (ATCC 25175) and one of normal oral flora, *Streptococcus oralis* (ATCC 9811) were cultured in a tryptic soy broth (TSB) medium (17 g of pancreatic digest of casein, 3 g of enzymatic digest of soybean meal, 2.5 g of dextrose, 5 g of sodium chloride, 2.5 g of dipotassium phosphate) at 37° C. under aerobic conditions for 24 hours.

Example 2: Preparation of Quorum Sensing (QS) Inhibitor Candidates

As candidates of the autoinducer-2 (AI-2) quorum sensing (QS) inhibitor (AI-2 Quorum Sensing Inhibitor, QSI), D-ribose (D-rib), D-galactose (D-gal), D-glucose (D-Glu), D-mannose (D-Man) and D-arabinose (D-ara) were prepared. D-ribose was purchased from Tokyo Chemical Industry Co. (Tokyo, Japan), and the others were purchased from Sigma-Aldrich (St. Louis, Mo., USA). Further, a synthetic compound, (5Z)-4-bromo-5-(bromomethylene)-2(5H)-furanone (furanone compound; Fur) was purchased from Sigma-Aldrich (St. Louis, Mo., USA) and prepared as a QSI candidate (a positive control).

Example 3: Test of Inhibitory Effect on Biofilm Formation by *F. nucleatum* (Fn)

*F. nucleatum* (Fn) is a major periodontopathogenic bacterium that functions as a mediator in the biofilm formation of periodontopathic bacteria and plays an important role in periodontal diseases.

To test biofilm formation by Fn, a Fn culture broth (2 ml; a negative control group, the number of bacteria: $2 \times 10^7$/ml), a mixture of Fn culture broth (2 ml) and *F. nucleatum* AI-2 (purified from *F. nucleatum* secretary material of *F. nucleatum* culture broth using a C18 Sep-Pak reverse-phase column (Waters Co., Milford, Mass.); hereinafter, referred to as 'Fn AI-2'; 10% (v/v) with respect to the total volume of the mixture with Fn culture broth), or a mixture of Fn culture broth (2 ml) and Fn AI-2 (10% (v/v) with respect to the total volume of the mixture with Fn culture broth) and each of QSI candidates was added to a 24-well plate with a glass slip (round, 12 mm radius), and cultured under anaerobic conditions for 48~72 hours. As the QSI candidates, sugars (D-rib, D-gal, D-Glu, D-Man, or D-ara) were used in an amount of 2 mM, and the furanone compound [(5Z)-4-bromo-5-(bromomethylene)-2(5H)-furanone] was used in an amount of 2 μM.

Biofilms formed on the cover slips were stained with 10% crystal violet [Tris(4-(dimethylamino)phenyl)methylium chloride] for 10 minutes, washed three times with PBS, and destained with 1 ml of acetone-alcohol (20:80, vol/vol). The optical density at 590 nm of the destaining solution containing crystal violet was measured using a microplate reader (a Wallac Victor3 microtiter, PerkinElmer Life Sciences, Waltham, Mass.). The smaller optical density ($OD_{590}$) measured at 590 nm represents more inhibition of biofilm formation, that is, higher quorum sensing inhibitory effect of the used QSI candidate.

The result of biofilm formation by Fn is given in the following Table 1 and FIG. 1.

TABLE 1

| Sample | $OD_{590\ nm}$ |
|---|---|
| None | 0 |
| Fn | 0.46 |
| Fn/AI-2 (negative control) | 1.5 |
| Fn/AI-2/Fur 2 µM | 0.49 |
| Fn/AI-2/D-gal 2 mM | 0.57 |
| Fn/AI-2/D-rib 2 mM | 0.77 |
| Fn/AI-2/D-glu 2 mM | 1.15 |
| Fn/AI-2/D-man 2 mM | 1.16 |
| Fn/AI-2/D-ara 2 mM | 1.37 |

As shown in Table 1 and FIG. 1, when only AI-2 was added to Fn, biofilm formation was increased. However, after addition of the QSI candidate such as D-gal, biofilm formation was inhibited. This result indicates that all sugars used as the QSI candidates have a significant QSI inhibitory effect, compared to the negative control group, and in particular, D-gal has excellent QSI inhibitory effect (inhibitory effect on biofilm formation) which is equivalent to that of the furanone compound.

Figure 2:
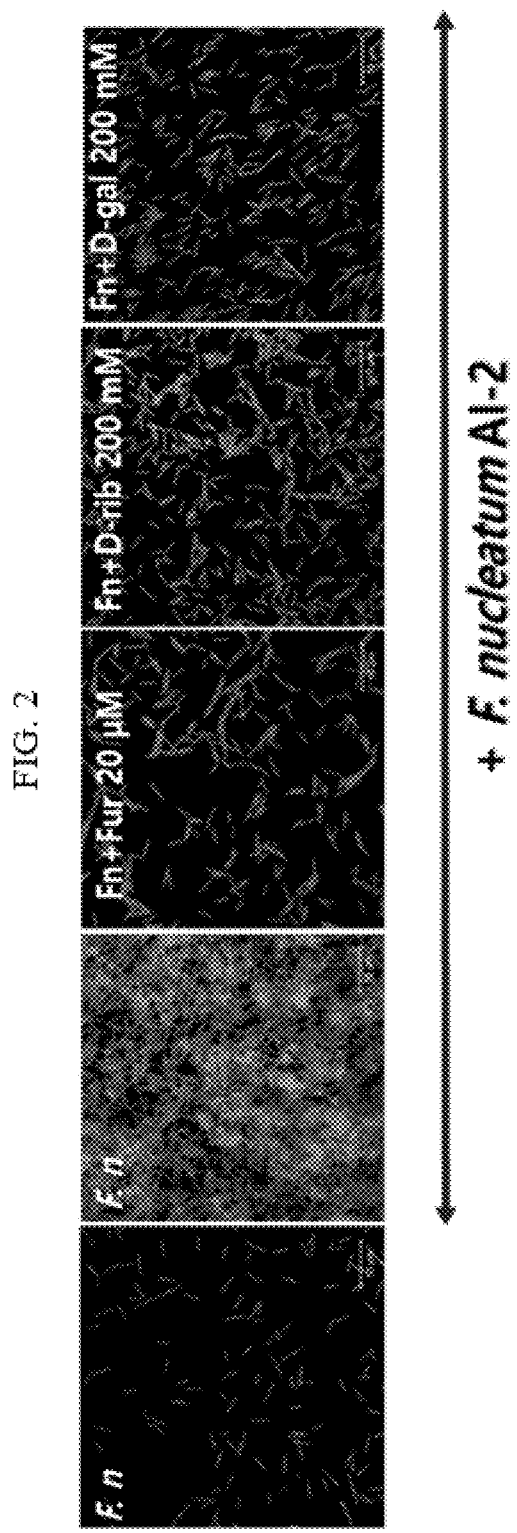
FIG. 2 is a fluorescence image showing results of fluorescence staining to examine inhibitory effects of quorum sensing inhibitor candidates on *F. nucleatum* (Fn) biofilm formation induced by Fn AI-2, in which live bacteria are indicated by light gray (bar: 10 μm)

Further, inhibitory effects of individual QSI candidates on Fn biofilm formation induced by Fn AI-2 were examined by fluorescence staining. 2 ml of Fn culture broth (the number of bacteria: $2\times10^7$/ml) was used, and Fn AI-2 was used in a volume of 10% (v/v) with respect to the total volume of a mixture with Fn culture broth. As the QSI candidates, 200 mM of D-rib or D-gal was used, and 20 µM of the furanone compound was used. Biofilms formed on the cover slip were stained with fluorescent materials using the live/dead-BacLight viability kit (Invitrogen, Grand Island, N.Y., USA) and observed using a confocal microscope (Carl Zeiss, LSM 700). The obtained fluorescence images are shown in FIG. 2. In the fluorescence images, live bacteria were stained with SYTO green to exhibit green fluorescence (indicated by light gray in FIG. 2), and dead bacteria were stained with propidium iodide (PI) to exhibit red fluorescence. Fluorescence intensities of the obtained individual fluorescence images were quantified using ZEN 2010 program of a confocal microscope, and shown in FIG. 3.

Figure 3:
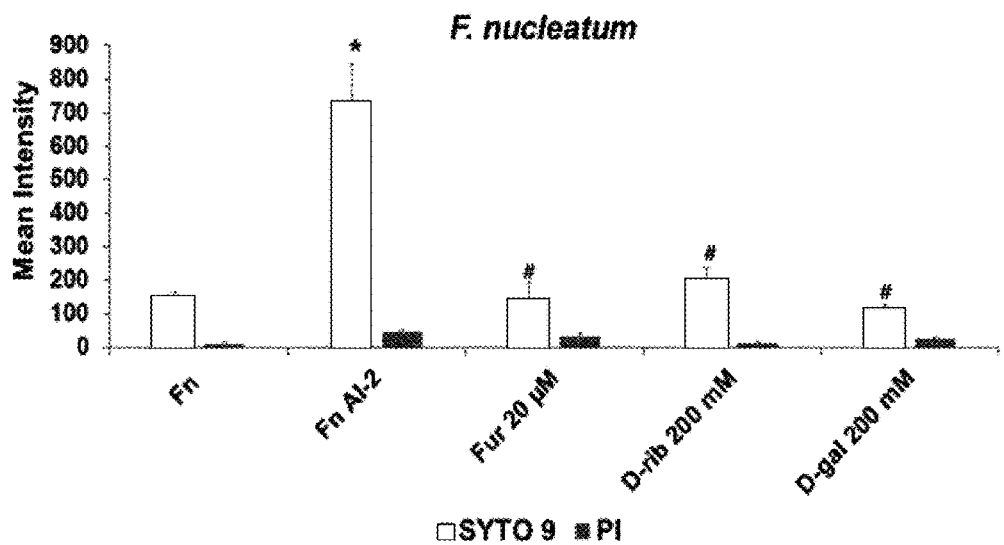
FIG. 3 is a graph showing quantification of fluorescence intensity of the fluorescence image of FIG. 2 (*: showing a statistical significance, compared to single Fn biofilm (indicated by 'Fn') ($p<0.05$); #: showing a statistical significance, compared to biofilm (indicated by 'Fn/AI-2') formed by addition of AI-2 to Fn ($p<0.05$))

As shown in FIGS. 2 and 3, the formed Fn biofilms were stained with fluorescence and then analyzed by confocal microscopy. As a result, consistent with the result of crystal violet staining, Fn biofilm formation was increased when only AI-2 was added to Fn, but Fn biofilm formation was inhibited when the QSI candidate such as D-gal or D-rib was added to Fn. In particular, D-gal showed a remarkably excellent inhibitory effect on Fn biofilm formation.

Example 4: Test of Inhibitory Effect on Biofilm Formation by *P. gingivalis*(Pg)

*P. gingivalis* (Pg) is known as a bacterium that is highly associated with periodontitis such as alveolar bone loss as well as systemic diseases such as arteriosclerosis.

To test biofilm formation by Pg, a test was performed in the same manner as in Example 3. That is, a Pg culture broth (2 ml; negative control group, the number of bacteria: $4\times10^8$/ml), a mixture of Pg culture broth (2 ml) and Fn AI-2 (10% (v/v) with respect to the total volume of the mixture with Pg culture broth), or a mixture of Pg culture broth (2 ml) and Fn AI-2 (10% (v/v) with respect to the total volume of the mixture with Fn culture broth) and D-gal (2 mM) was added to a 24-well plate with a glass slip (round, 12 mm radius), and cultured under anaerobic conditions for 48~72 hours. For comparison, 2 µM of the furanone compound [(5Z)-4-bromo-5-(bromomethylene)-2(5H)-furanone] was used instead of D-gal (2 mM) to perform the same test.

Biofilms formed on the cover slips were stained with 10% crystal violet [Tris(4-(dimethylamino)phenyl)methylium chloride] for 10 minutes, washed three times with PBS, and destained with 1 ml of acetone-alcohol (20:80, vol/vol). The optical density at 590 nm of the destaining solution containing crystal violet was measured using a microplate reader (a Wallac Victor3 microtiter, PerkinElmer Life Sciences, Waltham, Mass.). The smaller optical density ($OD_{590}$) measured at 590 nm represents more inhibition of biofilm formation, that is, higher quorum sensing inhibitory effect of the used QSI candidate.

The result of biofilm formation by Pg is given in the following Table 2 and FIG. 4.

TABLE 2

| Sample | $OD_{590\ nm}$ |
|---|---|
| None | 0 |
| Pg | 0.66 |
| Pg/AI-2 (negative control) | 2.00 |
| Pg/AI-2/Fur 2 µM | 0.98 |
| Pg/AI-2/D-gal 2 mM | 1.24 |

Figure 4:
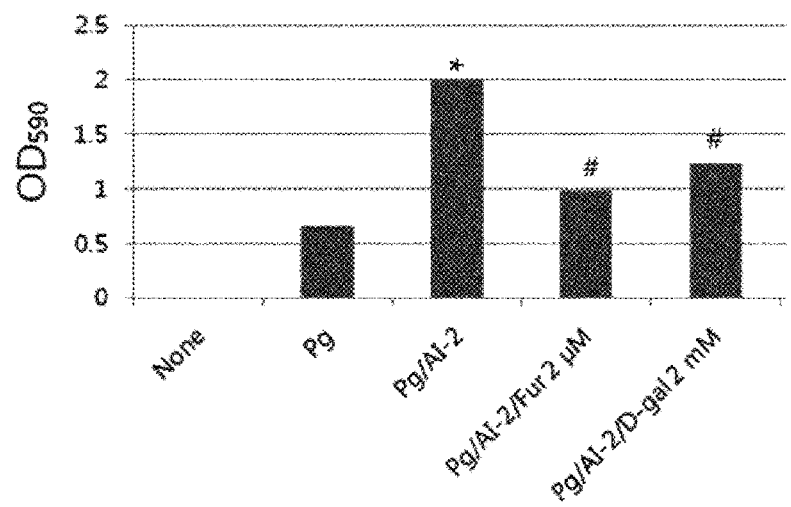
FIG. 4 is a graph showing result of crystal violet staining to examine inhibitory effects of quorum sensing inhibitor candidates on *P. gingivalis* (Pg) biofilm formation induced by Fn AI-2 (*: showing a statistical significance, compared to single Pg biofilm (indicated by 'Pg') ($p<0.05$); #: showing a statistical significance, compared to biofilm (indicated by 'Pg/AI-2') formed by addition of AI-2 to Pg ($p<0.05$))

As shown in Table 2 and FIG. 4, D-gal has an inhibitory effect on Pg biofilm formation, which is equivalent to that of the furanone compound.

Figure 5:
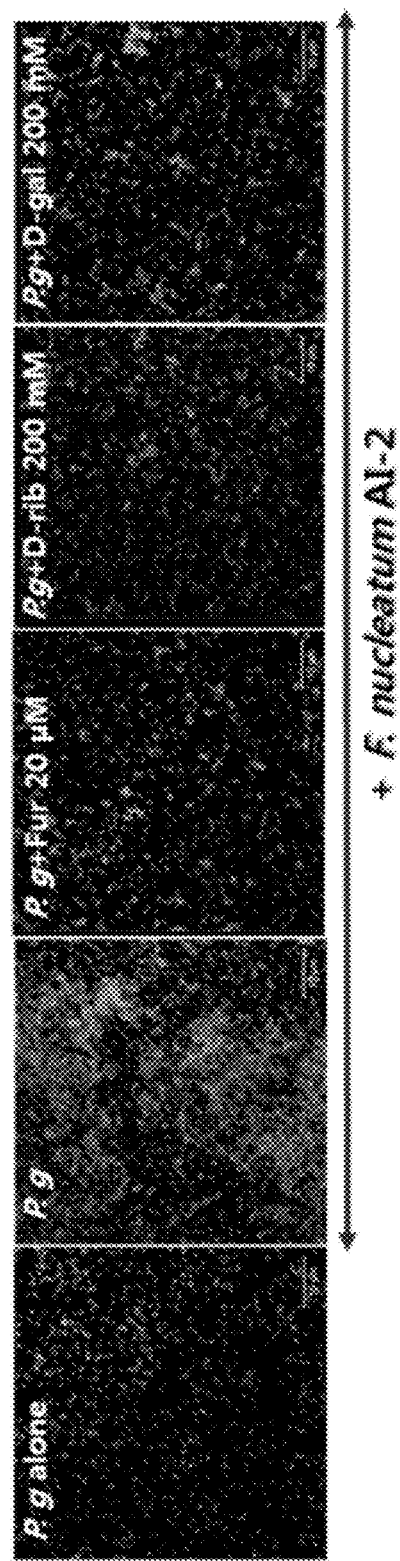
FIG. 5 is a fluorescence image showing result of fluorescence staining to examine inhibitory effects of quorum sensing inhibitor candidates on *P. gingivalis* (Pg) biofilm formation induced by Fn AI-2, in which live bacteria are indicated by light gray (bar: 10 μm)

Further, inhibitory effects of D-gal on Pg biofilm formation induced by Fn AI-2 were examined by fluorescence staining 2 ml of Pg culture broth (the number of bacteria: $4\times10^8$/ml) was used, and Fn AI-2 was used in a volume of 10% (v/v) with respect to the total volume of a mixture with Pg culture broth. 200 mM of D-gal was used, and for comparison, the same test was performed using 20 µM of the furanone compound, instead of D-gal. Biofilms formed on the cover slip were stained with fluorescent materials using the live/dead-BacLight viability kit (Invitrogen, Grand Island, N.Y., USA) and observed using a confocal microscope (Carl Zeiss, LSM 700). The obtained fluorescence images are shown in FIG. 5. In the fluorescence images, live bacteria were stained with SYTO green to exhibit green fluorescence (indicated by light gray in FIG. 5), and dead bacteria were stained with propidium iodide (PI) to exhibit red fluorescence. Fluorescence intensities of the obtained individual fluorescence images were quantified using ZEN 2010 program of a confocal microscope, and shown in FIG. 6.

Figure 6:
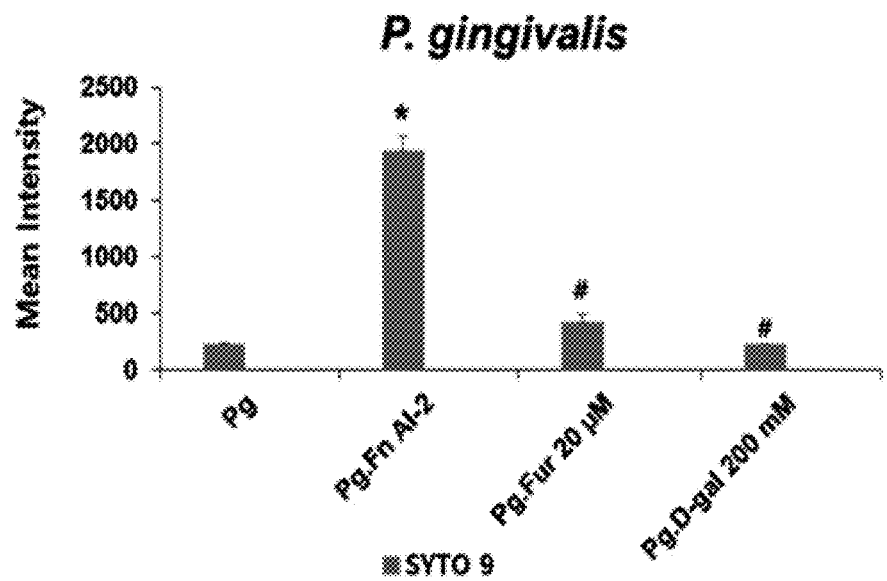
FIG. 6 is a graph showing quantification of fluorescence intensity of the fluorescence image of FIG. 5 (*: showing a statistical significance, compared to single Pg biofilm (indicated by 'Pg') ($p<0.05$); #: showing a statistical significance, compared to biofilm (indicated by 'Pg.FnAI-2') formed by addition of AI-2 to Pg ($p<0.05$))

As shown in FIGS. 5 and 6, the formed Pg biofilms were stained with fluorescence and then analyzed by confocal microscopy. As a result, consistent with the result of crystal violet staining, Pg biofilm formation was increased when only AI-2 was added to Pg, but Pg biofilm formation was inhibited when the QSI candidate such as D-gal was added to Pg. D-gal was found to have an inhibitory effect on Pg biofilm formation, which is equivalent to that of the furanone compound.

Example 5: Test of Inhibitory Effect on Biofilm Formation by T. forsythia (Tf)

*T. forsythia* (Tf) is one of the red-complex bacteria showing the highest pathogenicity in the periodontal tissue.

To test biofilm formation by Tf, a test was performed in the same manner as in Example 3. That is, a Tf culture broth (2 ml; a negative control group, the number of bacteria: $2 \times 10^8$/ml), a mixture of Tf culture broth (2 ml) and Fn AI-2 (10% (v/v) with respect to the total volume of the mixture with Tf culture broth), or a mixture of Tf culture broth (2 ml) and Fn AI-2 (10% (v/v) with respect to the total volume of the mixture with Tf culture broth) and D-gal (2 mM) was added to a 24-well plate with a glass slip (round, 12 mm radius), and cultured under anaerobic conditions for 48~72 hours. For comparison, 2 mM of D-rib or 2 μM of the furanone compound [(5Z)-4-bromo-5-(bromomethylene)-2 (5H)-furanone] was used instead of D-gal to perform the same test.

Biofilms formed on the cover slips were stained with 10% crystal violet [Tris(4-(dimethylamino)phenyl)methylium chloride] for 10 minutes, washed three times with PBS, and destained with 1 ml of acetone-alcohol (20:80, vol/vol). The optical density at 590 nm of the destaining solution containing crystal violet was measured using a microplate reader (a Wallac Victor3 microtiter, PerkinElmer Life Sciences, Waltham, Mass.). The smaller optical density ($OD_{590}$) measured at 590 nm represents more inhibition of biofilm formation, that is, higher quorum sensing inhibitory effect of the used QSI candidate.

The result of biofilm formation by Tf is given in the following Table 3 and FIG. 7.

TABLE 3

| Sample | $OD_{590 \, nm}$ |
|---|---|
| None | 0 |
| Tf | 0.32 |
| Tf/AI-2 (negative control) | 0.48 |
| Tf/AI-2/Fur 2 μM | 0.35 |
| Tf/AI-2/D-gal 2 mM | 0.2 |
| Tf/AI-2/D-rib 2 mM | 0.41 |

Figure 7:
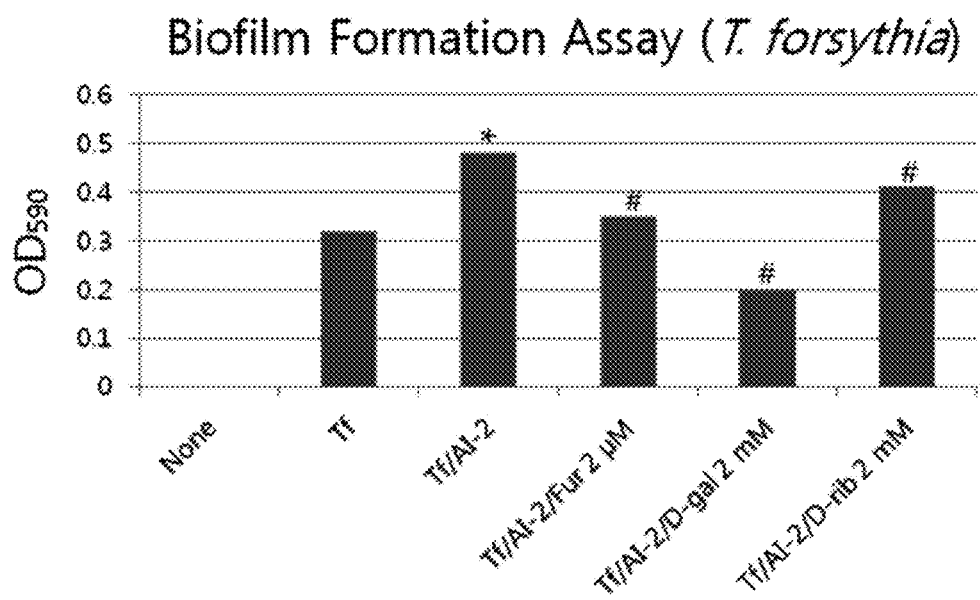
FIG. 7 is a graph showing results of crystal violet staining to examine inhibitory effects of quorum sensing inhibitor candidates on *T. forsythia* (Tf) biofilm formation induced by Fn AI-2 (*: showing a statistical significance, compared to single Tf biofilm (indicated by 'Tf') ($p<0.05$); #: showing a statistical significance, compared to biofilm (indicated by 'Tf/AI-2') formed by addition of AI-2 to Tf ($p<0.05$))

As shown in Table 3 and FIG. 7, D-gal and D-rib showed a significant inhibitory effect on Tf biofilm formation, and in particular, D-gal showed excellent inhibitory effect on Tf biofilm formation.

Figure 8:
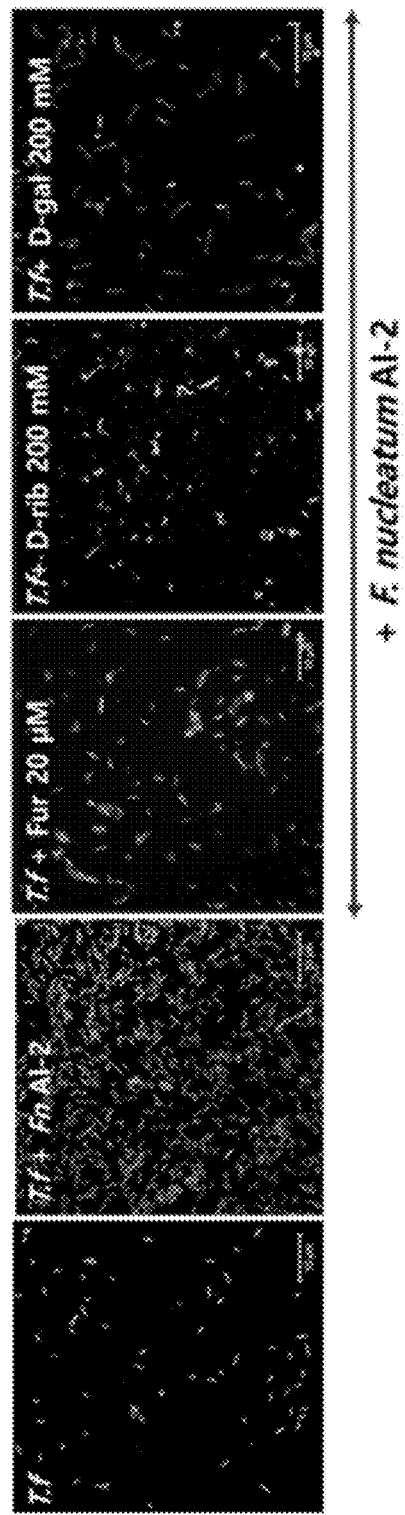
FIG. 8 is a fluorescence image showing results of fluorescence staining to examine inhibitory effects of quorum sensing inhibitor candidates on *T. forsythia* (Tf) biofilm formation induced by Fn AI-2 (bar: 10 μm)

Further, inhibitory effects of individual QSI candidates on Tf biofilm formation induced by Fn AI-2 were examined by fluorescence staining. 2 ml of Tf culture broth (the number of bacteria: $2 \times 10^8$/ml) was used, and Fn AI-2 was used in a volume of 10% (v/v) with respect to the total volume of a mixture with Tf culture broth. As the QSI candidates, 200 mM of D-rib or D-gal was used, and 20 μM of the furanone compound was used. Biofilms formed on the cover slip were stained with fluorescent materials using the live/dead-BacLight viability kit (Invitrogen, Grand Island, N.Y., USA) and observed using a confocal microscope (Carl Zeiss, LSM 700). The obtained fluorescence images are shown in FIG. 8. In the fluorescence images, live bacteria were stained with SYTO green to exhibit green fluorescence, and dead bacteria were stained with propidium iodide (PI) to exhibit red fluorescence. Fluorescence intensities of the obtained individual fluorescence images were quantified using ZEN 2010 program of a confocal microscope, and shown in FIG. 9.

Figure 9:
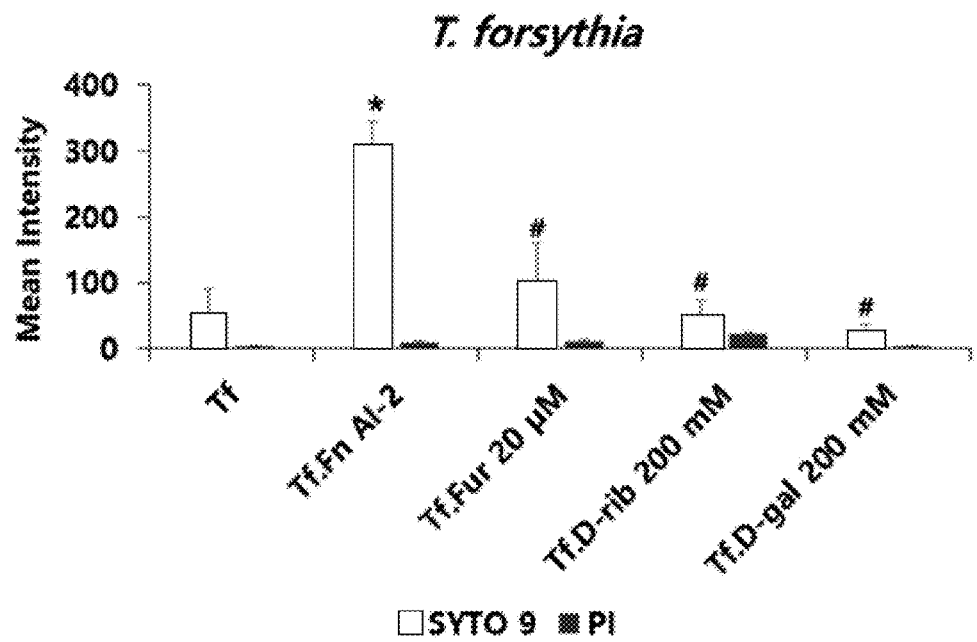
FIG. 9 is a graph showing quantification of fluorescence intensity of the fluorescence image of FIG. 8 (*: showing a statistical significance, compared to Tf biofilm (indicated by 'Tf') ($p<0.05$); #: showing a statistical significance, compared to biofilm (indicated by 'Tf.FnAI-2') formed by addition of AI-2 to Tf ($p<0.05$))

As shown in FIGS. 8 and 9, the formed Tf biofilms were stained with fluorescence and then analyzed by confocal microscopy. As a result, consistent with the result of crystal violet staining, Tf biofilm formation was increased when only AI-2 was added to Tf, but Tf biofilm formation was inhibited when the QSI candidate such as D-gal or D-rib was added. In particular, D-gal was found to have the most excellent inhibitory effect on Tf biofilm formation.

Example 6: Test of Inhibitory Effect on P. gingivalis (Pg) or T. forsythia (Tf) Biofilm Formation Induced by F. nucleatum (Fn) Secretory Material Using Transwell In order to examine efficacies of quorum sensing inhibitor (QSI) candidates on biofilm formation of periodontopathogenic bacteria which is induced by a secretory material of *F. nucleatum* (Fn), a test was performed using a transwell system. AI-2 naturally secreted by Fn is contained in the secretory material of Fn. Therefore, in the test using the transwell system, Fn AI-2 was not directly added to bacteria, but Fn was put in an upper chamber and Pg or Tf was put in a lower chamber. Biofilms cultured and formed in the presence or absence of QSI candidates were stained with crystal violet, followed by analysis. These conditions are to evaluate whether Pg or Tf biofilm formation is influenced by not a purified AI-2 but an AI-2-containing secretory material naturally secreted by Fn, and whether QSI candidates such as D-gal is able to inhibit the biofilm formation if the biofilm is then formed.

More specifically, the transwell system (24-well) has an upper chamber and a lower chamber which are separated from each other by a membrane of 0.4 μm. 500 μl of *F. nucelatum* (Fn) culture broth (the number of bacteria: $2 \times 10^7$ CFU/ml) was cultured in the upper chamber. A glass slip placed in the lower chamber, and then the same number of *P. gingivalis*(Pg) or *T. forsythia*(Tf) was inoculated in 1 ml of medium and cultured for 48~72 hours. The same QSI candidates were added to the upper and lower chambers. As the QSI candidates, 2 mM of sugar (D-rib or D-gal) was used and 2 μM of the furanone compound [(5Z)-4-bromo-5-(bromomethylene)-2(5H)-furanone] was used. In order to examine whether biofilm formation of the bacteria in the lower chamber is influenced by Fn secretory material and QSI candidates, the biofilms formed on the glass slip were stained with crystal violet, and then quantified (see Examples 3 to 5).

Figure 10:
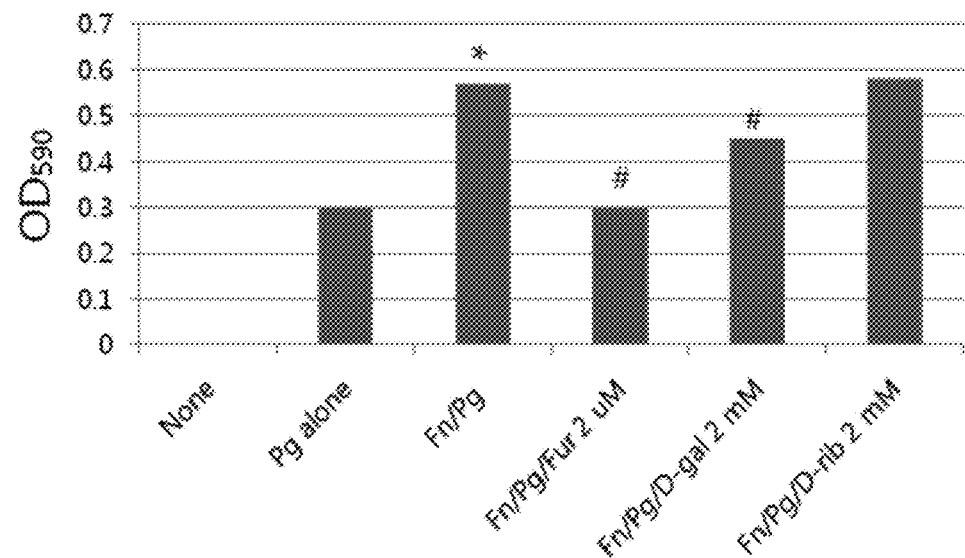
FIG. 10 is a graph showing result of crystal violet staining to examine inhibitory effects of quorum sensing inhibitor candidates on *P. gingivalis* (Pg) biofilm formation induced by an Fn secretory material (*: showing a statistical significance, compared to single Pg biofilm (indicated by 'Pg alone') ($p<0.05$); #: showing a statistical significance, compared to biofilm (indicated by 'Fn/Pg/AI-2') formed by addition of the Fn secretory material to Pg ($p<0.05$))

The result obtained after culturing Pg in the lower chamber is given in Table 4 and FIG. 10.

TABLE 4

| Sample | $OD_{590 \, nm}$ |
|---|---|
| None | 0 |
| Pg alone | 0.30 |
| Fn/Pg | 0.57 |
| Fn/Pg/Fur 2 μM | 0.30 |
| Fn/Pg/D-gal 2 mM | 0.45 |
| Fn/Pg/D-rib 2 mM | 0.58 |

Figure 11:
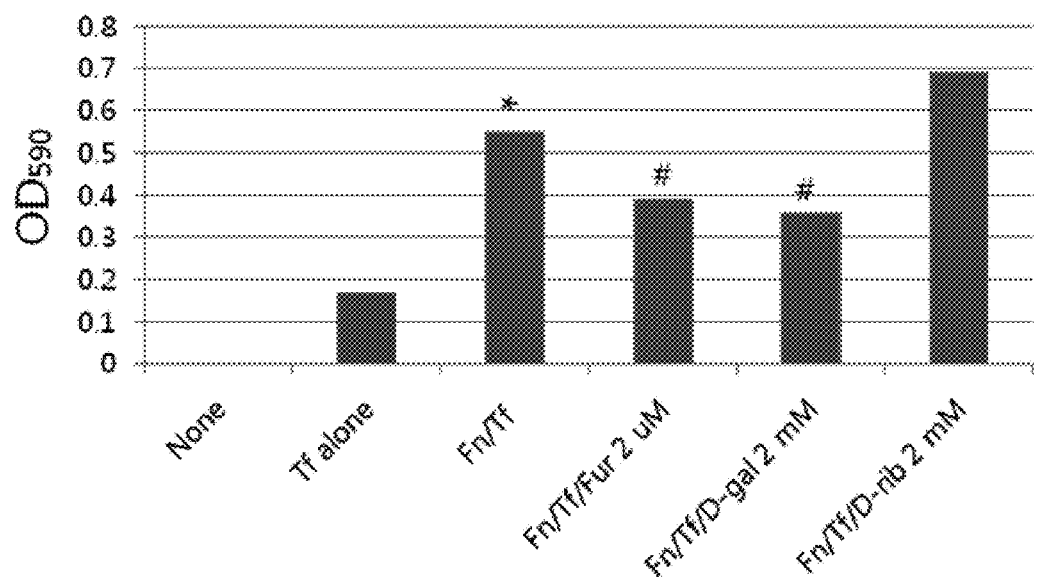
FIG. 11 is a graph showing results of crystal violet staining to examine inhibitory effects of quorum sensing inhibitor candidates on *T. forsythia* (Tf) biofilm formation induced by an Fn secretory material (*: showing a statistical significance, compared to single Tf biofilm (indicated by 'Tf alone') ($p<0.05$); #: showing a statistical significance, compared to biofilm (indicated by 'Fn/Tf/AI-2') formed by addition of the Fn secretory material to Tf ($p<0.05$))

Further, the result obtained after culturing Tf in the chamber is given in Table 5 and FIG. 11.

TABLE 5

| Sample | $OD_{590}$ |
|---|---|
| None | 0 |
| Tf alone | 0.17 |

TABLE 5-continued

| Sample | OD$_{590}$ |
| --- | --- |
| Fn/Tf | 0.55 |
| Fn/Tf/Fur 2 μM | 0.39 |
| Fn/Tf/D-gal 2 mM | 0.36 |
| Fn/Tf/D-rib 2 mM | 0.69 |

As shown in Tables 4 and 5 and FIGS. 10 and 11, Pg or Tf biofilm formation was increased by Fn secretory material, but inhibited by treatment of D-gal. D-gal was found to have a remarkably excellent inhibitory effect, compared to D-rib.

Example 7: Test of Inhibitory Activity of D-Galactose on AI-2 Activity

In this Example, it was demonstrated that D-galactose showing the most excellent inhibitory effect on biofilm formation in Examples 3-6 exhibits the effect not by killing the bacteria or inhibiting adhesion between bacteria to inhibit aggregation between bacteria or biofilm formation but by inhibiting quorum sensing between bacteria.

The quorum sensing autoinducer, AI-2 stimulates luciferase operon (lux genes) of *V. harveyi* to induce luciferase expression, resulting in luminescence. Therefore, inhibition of AI-2 activity was confirmed by measuring bioluminescence by AI-2. Bioluminescence mediated by AI-2 was determined using the AI-2 reporter strain *V. harveyi* BB170. *V. harveyi* BB170 was cultured in AB medium overnight at 30° C. until OD600 nm=0.7. The bacteria were washed with fresh AB medium and diluted to a concentration of $10^6$ cells/ml. Thereafter, *V. harveyi* BB170 culture broth (5 ml) was mixed with a partially purified *F. nucleatum* AI-2('Fn AI-2') and D-gal (0 or 20 mM) or D-rib (0 or 20 mM). The partially purified Fn AI-2 was obtained by partially purifying the Fn culture broth using a C18 Sep-Pak reverse-phase column (Waters Co., Milford, Mass.). The Fn culture broth or the partially purified Fn AI-2 was added such that a final concentration of AI-2 in the mixture was 10% (vol/vol). 10% (v/v) of Fn AI-2 corresponds to the Fn bacterial number of $1.9 \times 10^8$. Then, culture was performed at 30° C. for 1-8 hours. The bioluminescence was measured using a luminometer (GloMax1-Multi detection System, Promega, Madison, Wis.). BB170 is one of *V. harveyi* bacteria which have a characteristic of recognizing AI-2 to show bioluminescence. The higher bioluminescence value thus measured represents higher AI-2 activity.

Figure 12:
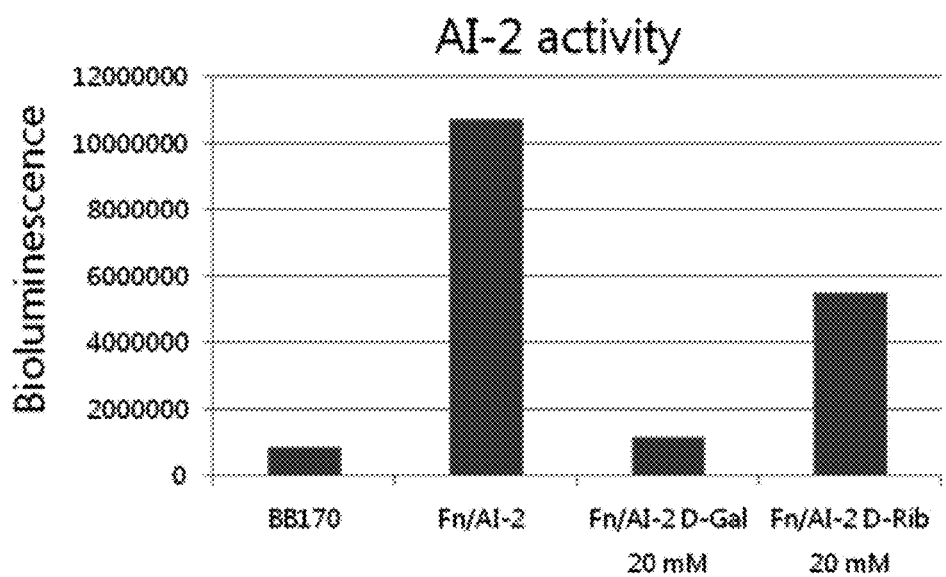
FIG. 12 is a graph showing bioluminescence measured after treatment of *V. harveyi* BB170 with Fn AI-2 and quorum sensing inhibitor candidates, in which lower bioluminescence indicates higher inhibitory activity of Fn AI-2.

The obtained result is given in Table 6 and FIG. 12.

TABLE 6

| Sample | Bioluminescence |
| --- | --- |
| BB170 | 856873 |
| Fn/AI-2 | 10712312 |
| Fn/AI-2 D-gal 20 mM | 1138752 |
| Fn/AI-2 D-rib 20 mM | 5481975 |

As shown in Table 6 and FIG. 12, when D-gal was added, bioluminescence was remarkably reduced (about 20% of the bioluminescence upon addition of D-rib), indicating that D-gal is a quorum sensing inhibitor inhibiting AI-2 activity.

Quorum sensing is an essential process for biofilm formation and virulence expression of bacteria causing dental caries and periodontal disease. In this Example, therefore, it is suggested that D-galactose is an excellent quorum sensing inhibitor inhibiting AI-2 activity, and thus biofilm formation and virulence expression are inhibited by this action, and D-galactose is also a material capable of widely controlling biofilm formation and periodontal diseases over the limitation of simply inhibiting aggregation between Fn and several bacteria.

Example 8: Effect of D-Galactose on Bacterial Growth

In this Example, an effect of D-galactose, in which D-galactose showed the most excellent inhibitory effect on biofilm formation in Examples 3-6, on bacterial growth was tested.

In detail, *F. nucleatum* was cultured in the presence of 0 mM (control group) and 100 mM of D-galactose at 37° C. under anaerobic conditions for 24~48 hours, and then optical density at 600 nm was determined to measure cell growth.

Figure 13:
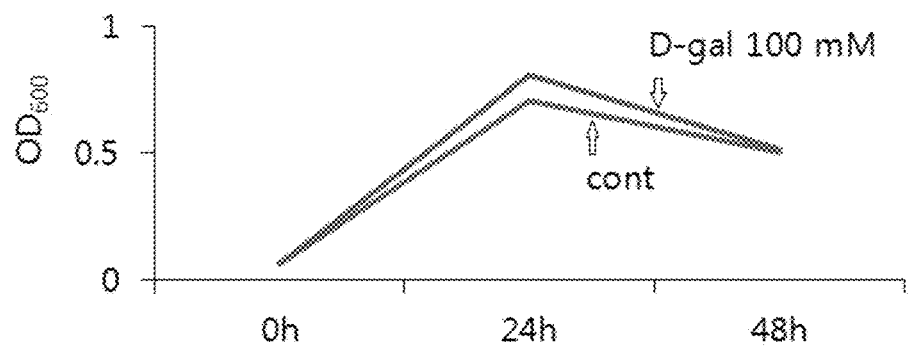
FIG. 13 is a growth curve of *F. nucleatum* treated with D-gal or not.

The obtained result is shown in FIG. 13. As shown in FIG. 3, when D-gal was added, a cell growth curve showed a similar pattern to a control group (Cont) added with no D-gal, indicating that D-gal does not directly kill bacteria and does not affect bacterial growth.

Example 9: Inhibitory Efficacy of D-Galactose on Biofilm Formation of Cariogenic Bacteria According to a recent report, dental caries is caused not by a single species *S. mutans* (Sm) which is known as a representative cariogenic bacterium but by biofilms formed by several species of bacteria (*mutans streptococcus*) having a similar feature. The cariogenic bacterium Sm expresses glucosyl transferase and glucan binding protein, which promote adherence of bacteria to salivary pellicle-coated tooth surfaces, on its surface, and also secretes them to the peripheral regions. Therefore, a larger number of bacteria bind to Sm adhered to teeth to develop biofilms, thereby accumulating a bacterial metabolite, lactic acid. As a result, pH around the teeth is decreased to 5.5 or lower to cause tooth decay, leading to dental caries.

In this Example, from the above known facts, it was inferred that the biofilm formation and secretion of highly acidic substance causing dental caries are mediated by AI-2, and it was tested whether D-gal previously found to inhibit biofilm formation of periodontopathogenic bacteria exhibits its efficacy on cariogenic bacteria.

2 mL ($2 \times 10^7$/ml) of the culture broth of a representative cariogenic bacterium *S. mutans* (Sm) and 2 mL ($2 \times 10^7$/ml) of the culture broth of one of normal oral flora, *S. oxalis* (SO) were added to a saliva-coated glass slip (round, 12 mm radius), respectively and cultured with 0 mM or 2 mM of D-galactose to form biofilms. The formed biofilms were stained with crystal violet in the same manner as in Examples 3-6 to test biofilm formation according to the presence of D-galactose. Further, the biofilms were stained with fluorescent materials using the live/dead-BacLight viability kit (Invitrogen, Grand Island, N.Y., USA), followed by analysis. For comparison, 2 μM of the furanone compound was used instead of D-galactose to perform the same test.

The result of biofilm formation by Sm is given in the following Table 7 and FIG. 14.

TABLE 7

| Sample | OD$_{590\ nm}$ |
| --- | --- |
| None | 0 |
| Sm | 0.48 |

TABLE 7-continued

| Sample | $OD_{590\,nm}$ |
|---|---|
| Sm/Fur 2 μM | 0.51 |
| Sm/D-gal 2 mM | 0.37 |

Figure 14:
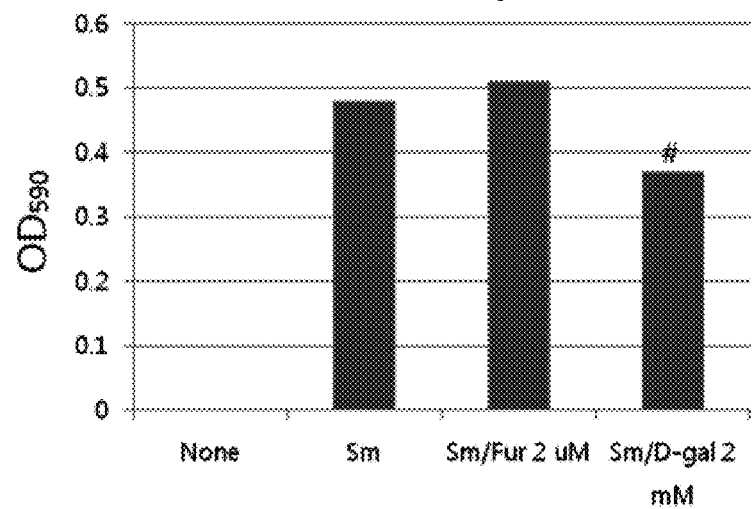
FIG. 14 is a graph showing results of crystal violet staining to examine inhibitory effect of D-gal on *S. mutans* (Sm) biofilm formation (*: showing a statistical significance, compared to single Sm biofilm (indicated by 'Sm') ($p<0.05$)

As shown in Table 7 and FIG. 14, the furanone compound hardly exhibited the inhibitory effect on Sm biofilm formation, whereas D-gal exhibited the significant inhibitory effect on Sm biofilm formation.

Figure 15:
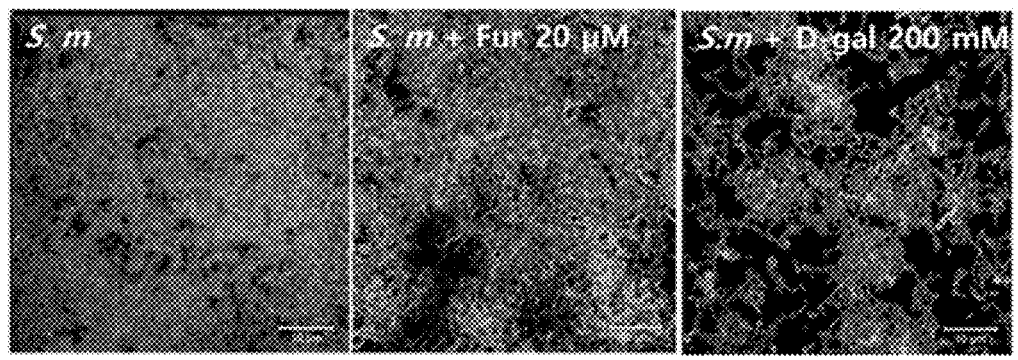
FIG. 15 is a fluorescence image showing result of fluorescence staining to examine inhibitory effect of D-gal on biofilm formation of *S. mutans* (Sm) (bar: 10 μm)

Further, the inhibitory effect of D-gal on Sm biofilm formation was examined by fluorescent staining. 2 ml ($2\times10^7$/ml) of Sm culture broth was used, and 200 mM of D-gal and 20 μM of the furanone compound were used. Biofilms formed on the cover slip were stained with fluorescent materials using the live/dead-BacLight viability kit (Invitrogen, Grand Island, N.Y., USA) and observed using a confocal microscope (Carl Zeiss, LSM 700). The obtained fluorescence images are shown in FIG. 15. In the fluorescence images, live bacteria were stained with SYTO green to exhibit green fluorescence, and dead bacteria were stained with propidium iodide (PI) to exhibit red fluorescence. Fluorescence intensities of the obtained individual fluorescence images were quantified using ZEN 2010 program of a confocal microscope, and shown in FIG. 16.

Figure 16:
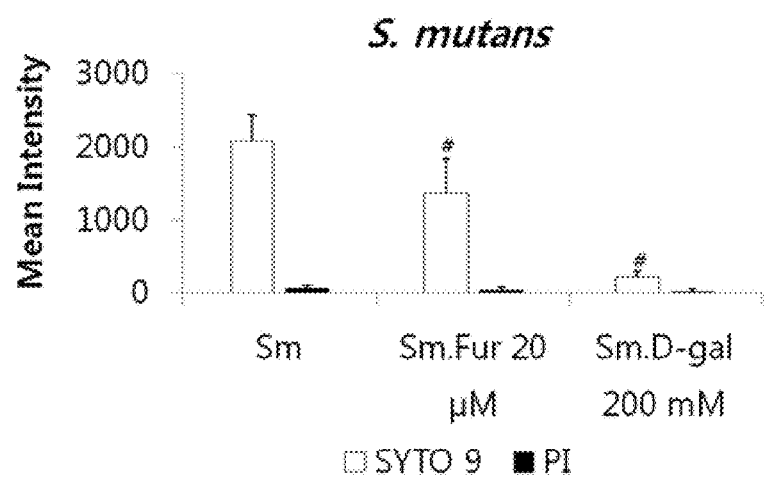
FIG. 16 is a graph showing quantification of fluorescence intensity of the fluorescence image of FIG. 15 (#: showing a statistical significance, compared to *S. mutans* (Sm) ($p<0.05$))

As shown in FIGS. 15 and 16, the formed Sm biofilms were stained with fluorescence and then analyzed by confocal microscopy. As a result, consistent with the result of crystal violet staining, Sm biofilm formation was inhibited by treatment of D-gal, and this inhibitory effect of D-gal on Sm biofilm formation was superior to that of the furanone compound.

Further, the result of biofilm formation by So is given in the following Table 8 and FIG. 17.

TABLE 8

| Sample | $OD_{590}$ |
|---|---|
| None | 0 |
| So | 0.59 |
| So/Fur 2 uM | 0.64 |
| So/D-gal 2 mM | 1.07 |
| So/D-rib 2 mM | 0.85 |

Figure 17:
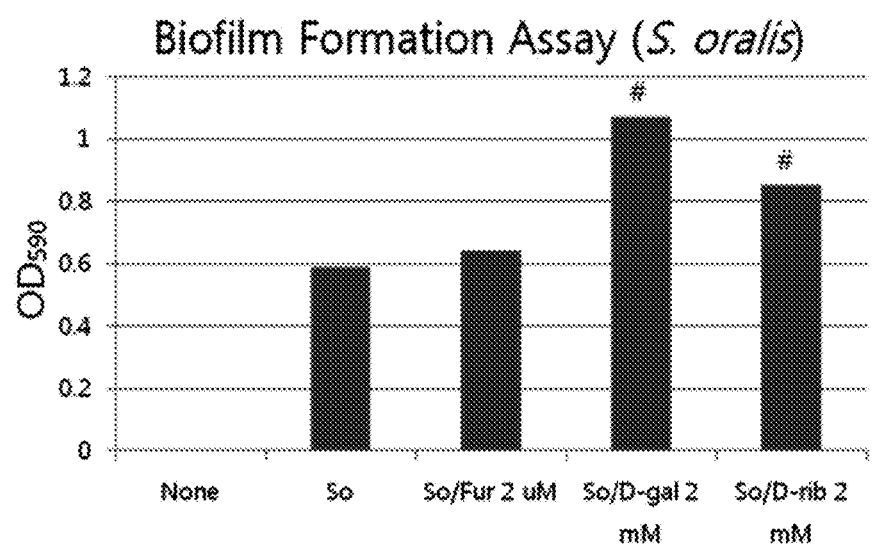
FIG. 17 is a graph showing result of crystal violet staining to examine inhibitory effect of D-gal on biofilm formation of *S. oralis* (So) (*: showing a statistical significance, compared to single So biofilm (indicated by 'So') ($p<0.05$).

As shown in Table 8 and FIG. 17, D-gal did not inhibit but increased biofilm formation by one of normal oral flora, Streptococcus oralis (So), compared to D-rib and the furanone compound.

As shown in Tables 7 and 8 and FIGS. 14 to 17, D-galactose significantly inhibited biofilm formation by a cariogenic bacterium Sm, whereas it did not inhibit but increased biofilm formation by one of normal oral flora, Streptococcus oralis (So). To maintain oral health, it is important to maintain the normal oral flora without inhibition thereof.

The results of Examples 1-9 suggest that D-galactose exhibits superior inhibitory efficacy on biofilm formation by bacteria causing two representative oral diseases, periodontitis and dental caries, and further, it did not affect biofilm formation by normal oral flora. Therefore, D-galactose is a superior substance which can be selectively applied to periodontopathogenic bacteria.

What is claimed is:

1. A method of inhibiting quorum sensing of oral disease-causing bacteria, the method comprising administering toothpaste containing D-galactose in an amount of 0.036 to 3.6% by weight to a buccal mucosa, a tooth, a gingiva, or a tongue of a subject in need of inhibition of quorum sensing of oral disease-causing bacteria,
    wherein the oral disease-causing bacteria is *Streptococcus mutans*, and the D-galactose does not inhibit quorum sensing of non-pathogenic normal oral flora which is one or more selected from the group consisting of *Streptococcus oralis*, *Streptococcus salivarius*, and *Streotpcoccus mitis*.

2. A method of inhibiting quorum sensing autoinducers of oral disease-causing bacteria, the method comprising administering toothpaste containing D-galactose in an amount of 0.036 to 3.6% by weight to a buccal mucosa, a tooth, a gingiva, or a tongue of a subject in need of inhibition of quorum sensing autoinducers of oral disease-causing bacteria,
    wherein the oral disease-causing bacteria is *Streptococcus mutans*, and the D-galactose does not inhibit quorum sensing autoinducer of non-pathogenic normal oral flora which is one or more selected from the group consisting of *Streptococcus oralis*, *Streptococcus salivarius*, and *Streotpcoccus mitis*.

3. A method of inhibiting biofilm formation of oral disease-causing bacteria, the method comprising administering toothpaste containing D-galactose in an amount of 0.036 to 3.6% by weight to a buccal mucosa, a tooth, a gingiva, or a tongue of a subject in need of inhibition of biofilm formation of oral disease-causing bacteria,
    Wherein the oral disease-causing bacteria is *Streptococcus mutans*, and the D-galactose does not inhibit biofilm formation of non-pathogenic normal oral flora which is one or more selected from the group consisting of *Streptococcus oralis*, *Streptococcus salivarius*, and *Streotpcoccus mitis*.

4. A method of reducing virulence of oral disease-causing bacteria by inhibiting quorum sensing of the oral disease-causing bacteria, the method comprising administering toothpaste containing D-galactose in an amount of 0.036 to 3.6% by weight to a buccal mucosa, a tooth, a gingiva, or a tongue of a subject in need of reduction of virulence of oral disease-causing bacteria,
    wherein the oral disease-causing bacteria is *Streptococcus mutans*, and the D-galactose does not inhibit quorum sensing of non-pathogenic normal oral flora which is one or more selected from the group consisting of *Streptococcus oralis*, *Streptococcus salivarius*, and *Streotpcoccus mitis*.

5. A method of treating or ameliorating an oral bacterial disease by inhibiting quorum sensing of the oral disease-causing bacteria, the method comprising administering toothpaste containing D-galactose in an amount of 0.036 to 3.6% by weight to a buccal mucosa, a tooth, a gingiva, or a tongue of a subject in need of treating or ameliorating the oral bacterial disease,
    wherein the oral disease-causing bacteria is *Streptococcus mutans*, and the D-galactose does not inhibit quorum sensing of non-pathogenic normal oral flora which is one or more selected from the group consisting of *Streptococcus oralis*, *Streptococcus salivarius*, and *Streotpcoccus mitis*.

6. The method of claim 5, wherein the oral bacterial disease is dental caries.

* * * * *